(12) United States Patent
Moulin

(10) Patent No.: US 6,322,519 B1
(45) Date of Patent: Nov. 27, 2001

(54) RESPIRATORY PEAK-FLOW METER

(75) Inventor: Jacques Moulin, Saint Romans (FR)

(73) Assignee: Societe de Therformage et D'Injection des Plastiques-S.T.L., Beauvior en Royans (FR)

( * ) Notice: Subject to any disclaimer, the term of this patent is extended or adjusted under 35 U.S.C. 154(b) by 0 days.

(21) Appl. No.: 08/647,932

(22) PCT Filed: Sep. 26, 1995

(86) PCT No.: PCT/FR95/01234

§ 371 Date: Mar. 17, 2000

§ 102(e) Date: Mar. 17, 2000

(87) PCT Pub. No.: WO96/10360

PCT Pub. Date: Apr. 11, 1996

(30) Foreign Application Priority Data

Sep. 30, 1994 (FR) .................................................. 94 11976

(51) Int. Cl.[7] .......................................................... A61B 5/00
(52) U.S. Cl. ............................................ 600/538; 600/529
(58) Field of Search .................................... 128/716, 720, 128/724, 725, 727, 730; 600/509, 530, 532, 537, 538

(56) References Cited

U.S. PATENT DOCUMENTS

| | | |
|---|---|---|
| 3,608,546 | 9/1971 | Shinn . |
| 3,922,525 * | 11/1975 | Kozak et al. .................. 128/725 |
| 5,137,026 | 8/1992 | Waterson et al. . |
| 5,361,722 * | 11/1994 | Murnick et al. ................ 128/730 |
| 5,547,440 * | 8/1996 | Rubens et al. .................. 128/725 |
| 5,564,432 * | 10/1996 | Thomson ........................ 600/538 |

FOREIGN PATENT DOCUMENTS 0295575   12/1988   (EP) .

* cited by examiner

Primary Examiner—Robert L. Nasser
(74) Attorney, Agent, or Firm—McDermott, Will & Emery

(57) ABSTRACT

A device for measuring exhaled flow comprises a measuring tube partially obstructed by a narrow part of the tube; and a differential pressure sensor coupled to the tube for measuring the pressures inside the tube on either side of the narrow part. The measuring tube is removable and comprises, at its outer surface, flexible annular seals protruding from the outer surface and located on either side of openings which are in turn located on either side of the narrow part. The measuring tube is insertable in a recess of the device, the recess having a diameter slightly greater than the external diameter of the measuring tube such that, in an abutment position of the measuring tube in the recess, the annular seals define with the recess and the external wall of the tube annular chambers communicating respectively with two passages of the recess, connected to the pressure sensor.

2 Claims, 2 Drawing Sheets

RESPIRATORY PEAK-FLOW METER

BACKGROUND OF THE INVENTION

1. Field of the Invention

The present invention relates to an apparatus for measuring the lung characteristics of a patient. It more particularly addresses a portable spirometer for measuring various parameters which are necessary to the diagnostic of doctors, such as the peak-flow, the maximum exhaled volume per second, etc.

The peak-flow is often measured for people who suffer from asthma, bronchitis, mucoviscidosis, or who have been lung transplanted. Indeed, especially for those suffering from asthma, this measure allows the anticipation of an asthma crisis and, during treatment, allows the dosage of medicine intake.

It is thus desirable that the patients can regularly analyze their peak-flow, chart their characteristics and communicate these to their doctor or directly use them in a way prescribed by their doctor.

2. Description of the State of the Art

A known spirometer is of mechanical type, in which the breath of a patient acts on a spring biased piston. These mechanical devices have the advantage of being small and cheap but their main drawback is that they are little reliable, inaccurate and inconstant.

To realize an electronic flowmeter, it is known to use a Venturi flow sensor. Such a sensor comprises a tube with a narrow part. When a patient blows into the tube, a pressure difference establishes on both sides of the narrow part which is substantially proportional to the flow in a certain measuring range depending on the dimensions and the shape of the narrow part. This difference is measured by a differential pressure sensor connected through conduits to regions situated on either side of the narrow part.

A specific problem in the use of a Venturi flow sensor in a spirometer is connected to the fact that the spirometer must be regularly cleaned and sterilized, eventually after each use. In particular, the development of germs coming from saliva or other expectoration of the patient should be avoided in the tube and in the conduits which arrive to the sensor. Moreover, the cleaning is not easy because of the small functional passage at the narrow part and because of unavoidable corners and angles which are difficult to reach and which accumulate dirt.

U.S. Pat. No. 5,137,026 describes a portable electronic spirometer using such a Venturi flow sensor. The tube is integral with the casing of the device. To avoid dirt from going into the conduits which arrive to the pressure sensor, particular filters are placed in these conduits where they open into the tube. These filters must be liquid-tight and permeable to air. To clean and sterilize the tube, the whole device must be plunged in an antiseptic solution. Therefore, the device must be perfectly water-tight, which increases its price substantially.

SUMMARY OF THE INVENTION

An object of the present invention is to provide a portable electronic spirometer with no cleaning and sterilization problems.

Another object of the present invention is to provide such a spirometer which is small and easy to manipulate and put away.

These objects are achieved by removably arranging the tube such that it can be removed and put back easily.

The invention more specifically addresses a device for measuring exhaled flow comprising a measuring tube partially obstructed by a narrow part of the tube; and a differential pressure sensor coupled to the tube for measuring the pressures inside the tube on either side of the narrow part. The measuring tube is removable and comprises, at its outer surface, flexible annular seals protruding from the outer surface and located on either side of openings which are in turn located on either side of the narrow part. The measuring tube is insertable in a recess of the device, the recess having a diameter slightly greater than the external diameter of the measuring tube such that, in an abutment position of the measuring tube in the recess, the annular seals define with the recess and the external wall of the tube annular chambers communicating respectively with two passages of the recess, connected to the pressure sensor.

According to an embodiment of the invention, the recess is tapered and the external wall of the measuring tube is complementary to the recess by steps, a step transition being situated at the level of each annular seal.

According to an embodiment of the invention, the annular seals are rings placed in grooves of the measuring tube.

According to an embodiment of the invention, the recess comprises, at its end of smallest diameter, an internal shoulder for stopping and centering the end of smallest diameter of the measuring tube.

According to an embodiment of the invention, the device comprises an elongated casing whose longitudinal axis is parallel to the axis of the measuring tube.

According to an embodiment of the invention, the internal end of the measuring tube communicates with a horn for deviating the air flow in the tube towards a side.

According to an embodiment of the invention, the annular seals are flanges integral with the measuring tube.

BRIEF DESCRIPTION OF DRAWINGS

The foregoing and other objects, features and advantages of the present invention will be exposed in detail in the following exemplary non-limiting description of particular embodiments by referring to the attached figures, among which.

DESCRIPTION OF PREFERRED EMBODIMENTS

Figure 1:
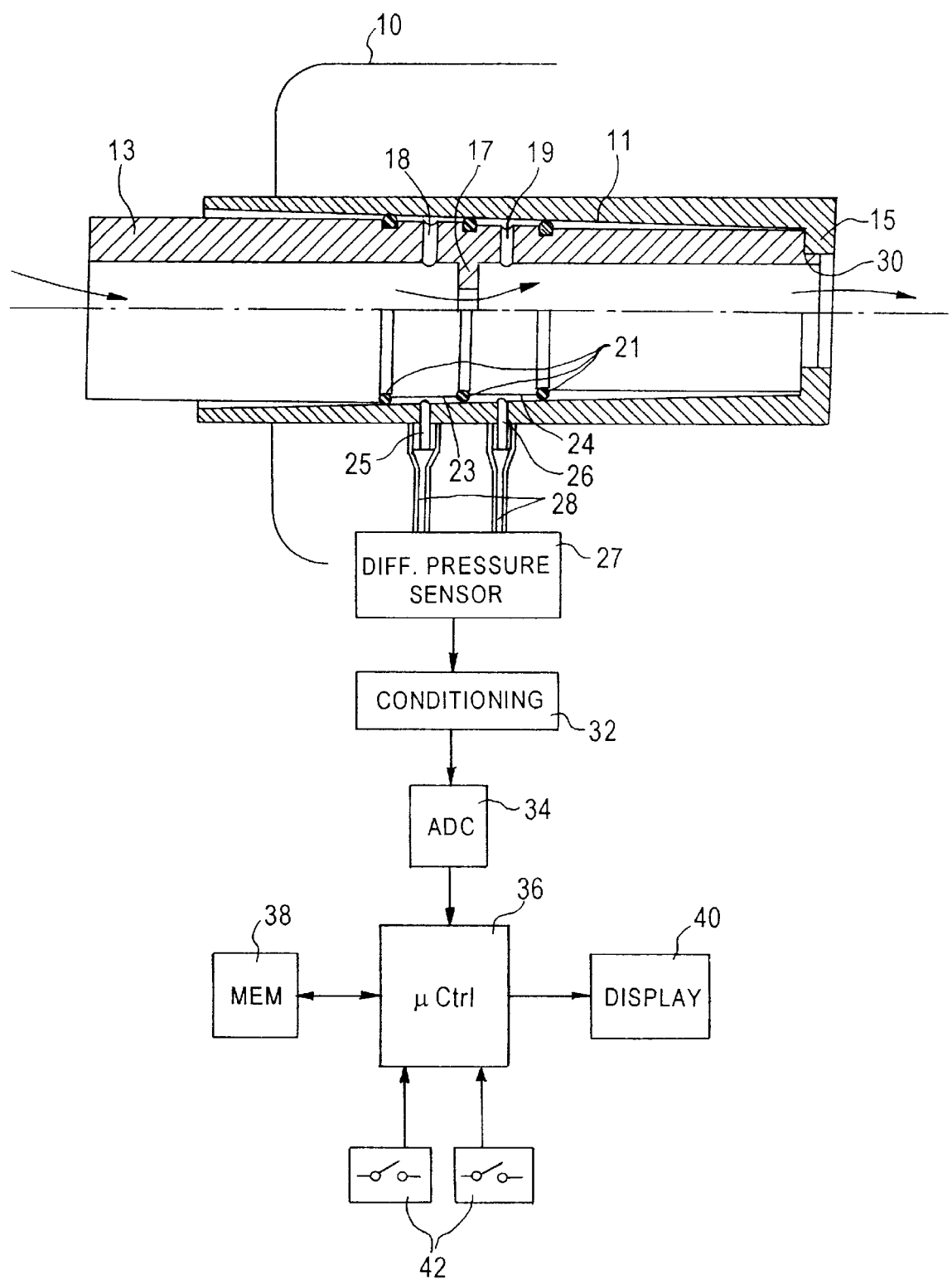
FIG. 1 shows an embodiment of a removable flow-measuring tube according to the present invention as well as, schematically, associated electronic circuitry.

FIG. 1 partially shows a spirometer casing 10 having, according to the invention, a cylindrical recess 11 with both its ends open to the atmosphere. This recess 11 is, for example, defined by the internal wall of a tube integral with casing 10. Inside recess 11, a removable measuring tube 13 is placed, whose external diameter is slightly smaller than the diameter of recess 11.

The measuring tube 13 is shown in its measuring position. One of its ends (on the left) protrudes out of recess 11 and constitutes a mouth-piece through which the patient blows. The other end of tube 13 abuts against an internal shoulder 15 of recess 11. This shoulder 15 can be situated anywhere in casing 10.

The measuring tube 13 is open at both its ends such that the air blown by the patient can freely flow from one end to the other of measuring tube 13, as shown by arrows. The measuring tube 13 is a diaphragm or Venturi measuring tube. The internal diameter of tube 13 is substantially constant and has a local narrow part (or diaphragm) 17 proximate to the center of the tube. The wall of tube 13 has two openings 18, 19 on either side of narrow part 17. The relative positions of these openings 18, 19 has no importance and there can be several openings at each side of narrow part 17.

Between the openings 18, 19 and on either side of these openings, annular seal rings 21 are placed in external grooves of tube 13. These seal rings 21 slightly protrude from the external surface of tube 13 and contact the wall of recess 11 to limit therewith and with the external wall of tube 13 two annular chambers 23, 24 respectively communicating with openings 18, 19. Recess 11 is provided with two passages 25, 26 opening respectively in the two annular chambers 23, 24 and coupled to a differential pressure sensor 27 either directly or through flexible tubes 28.

With this arrangement, the cavities on either side of narrow part 17 are in air-tight communication with the pressure sensor 17 through the openings 18, 19, the annular chambers 23, 24 and finally the passages 25, 26. The chambers 23, 24 have a small cross-section area but nevertheless allow, independently of the position of openings 18, 19 with respect to passages 25, 26, a reliable transmission of the pressure inside tube 13 towards sensor 27 because there is no air flow from the tube towards the sensor.

In FIG. 1, the openings 18, 19 are shown opposite to the passages 25, 26 with respect to the axis of the tube, but they can of course be at any radial position, provided that their axial position is such that the passages 25, 26 communicate with their respective chambers 23, 24.

Tube 13 is held in recess 11 by simple adherence of seal rings 21. Thus, tube 13 can be extracted and put back without a particular maintaining means and without particular care, except to push tube 13 in abutment against the shoulder 15 which defines the correct positioning of chambers 23, 24 with respect to the passages 25, 26 connected to the pressure sensor. This allows a particularly quick and easy manipulation of measuring tube 13.

When the patient blows into tube 13, his saliva and eventual expectoration adhere to the internal wall of tube 13. The saliva can eventually penetrate in the openings 18, 19 but it is very unlikely that it reaches the wall of recess 11 because there is no air flow through the openings 18, 19. Thus, to efficiently clean and sterilize the device, just tube 13 is removed and washed or immersed in an antiseptic solution. It is unnecessary to wash the whole device to ensure satisfactory hygiene conditions. Thus, the device need not be water-tight.

The fact that measuring tube 13 is removable allows the doctor to dispose of several tubes to realize measures on successive patients. The tubes 13 are simple parts, thus cheap, which can be realized in molded plastic.

According to an embodiment, the wall of recess 11 is slightly tapered, the smallest diameter being at the side of shoulder 15. This allows, the external tube 13 being complementary, the removal and the engagement of tube 13 in recess 11 with little effort. Indeed, the seal rings 21 then rub against recess 11 only over a small distance while inserting and removing tube 13. The internal end of tube 13 may have, as shown, a centering shoulder 30 cooperating with the abutment shoulder 15.

According to another embodiment, recess 11 still being tapered, the external surface of tube 13 may be realized, as shown, by cylindrical portions of progressive diameters to approach a tapering complementary to that of recess 11. Each diameter step is located at the level one of the seal rings 21. This solution allows a simplification of the production of tube 13.

An electronic circuit, located in casing 10, for exploiting the signal from sensor 27 is shown very schematically by way of example. In FIG. 1, the differential sensor 27 may be a commercially available differential sensor, such as the one referenced MPX10D from Motorola. The signal provided by this sensor 27 is processed by a signal conditioner 32 (amplifier, filter, integrator, etc.) before reaching an analog-to-digital converter 34. The digital signal provided by converter 34 is exploited by a micro-controller 36 which may store the flow value in a memory 38 and display it on a display 40. Push buttons 42 serve to select several functions of micro-controller 36 others than the simple flow measure, for example, the display of the previously measured flows as well as the date and the time of these measures.

Figure 2A:
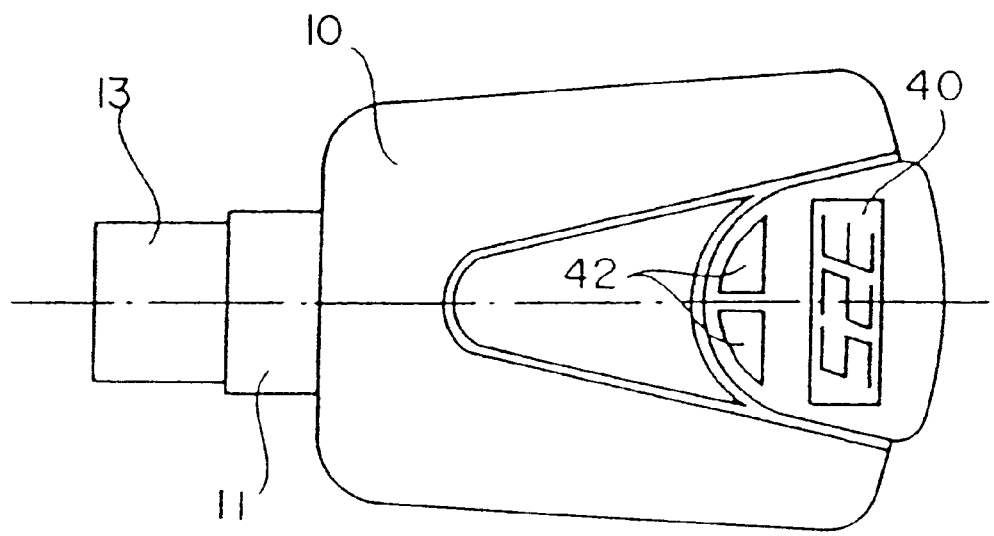
FIGS. 2A and 2B show a front view and a sectional side view of an embodiment of a whole portable spirometer according to the present invention.
Figure 2B:
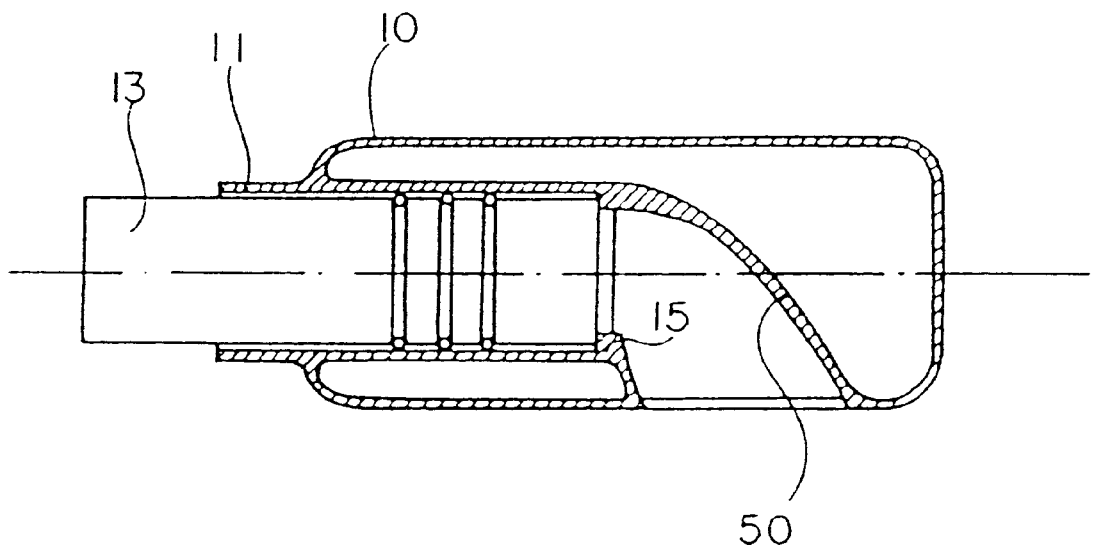

FIGS. 2A and 2B respectively show a front view and a sectional side view of an embodiment of the whole portable spirometer according to the invention.

In FIG. 2A, the casing 10 of the device is of trapezoidal shape with rounded corners. Tube 13 protrudes from the small side of the trapeze and recess 11 is constituted by a tube integral with casing 10. The display 40 is proximate to the large side of the trapeze and is placed parallel thereto. The buttons 42 are placed side by side under the display 40.

In FIG. 2B, the recess 11, at the level of shoulder 15, is extended by a horn 50, integral with casing 10, which deviates the air flow towards an opening of the bottom face of casing 10, i.e. perpendicularly to the axis of tube 13.

With this arrangement, the device is particularly small and can be easily put in a pocket, especially because no elongated part protrudes perpendicularly to the longitudinal axis of casing 10. The recess 11 and the horn 50 are easy to clean, if necessary, with a cloth or cotton wool wet with antiseptic solution. In practice, such a cleaning is carried out much less often than the cleaning of measuring tube 13.

The casing 10, integral with recess 11 and horn 50, is easy to produce in a single plastic molding operation.

Of course, several alternatives and modifications of the present invention will appear to those skilled in the art and the field of protection is defined by the scope of the attached claims.

A first alternative example concerns the sealing between the measuring tube and the recess. Instead of seal rings placed in grooves of the measuring tube, these seals can be small flanges integral with the tube. This alternative applies in particular to the production of plastic disposable tubes.

Another example of an alternative concerns the abutment between the measuring tube and its recess. Instead of an internal shoulder at one end of the recess, an external shoulder can be provided on the measuring tube, proximate to the mouth-peace.

What is claimed is:

1. A device for measuring exhaled flow comprising:

a measuring tube partially obstructed by a narrow part of the tube; and a differential pressure sensor coupled to the measuring tube for measuring pressure inside the measuring tube on either side of the narrow part, wherein the measuring the tube is removable from the device and comprises, at its outer surface, flexible annular seals protruding from the outer surface and located on either side of openings which are located on either side of the narrow part, the measuring tube being insertable in a recess of said device, said recess having a diameter slightly greater than an external diameter of the measuring tube such that, in an abutment position of the measuring tube in the recess, the annular seals define with the recess and an external wall of the measuring tube annular chambers communicating respectively with two passages of the recess, connected to the pressure sensor, and wherein the recess is tapered and the external wall of the measuring tube is complementary to the recess by steps, a step transition being situated at the level of each annular seal.

2. A device for measuring exhaled flow comprising:

a measuring tube partially obstructed by a narrow part of the tube; and a differential pressure sensor coupled to the measuring tube for measuring pressure inside the measuring tube on either side of the narrow part, wherein the measuring the tube is removable from the device and comprises, at its outer surface, flexible annular seals protruding from the outer surface and located on either side of openings which are located on either side of the narrow part, the measuring tube being insertable in a recess of said device, said recess having a diameter slightly greater than an external diameter of the measuring tube such that, in an abutment position of the measuring tube in the recess, the annular seals define with the recess and an external wall of the measuring tube annular chambers communicating respectively with two passages of the recess, connected to the pressure sensor, and wherein an internal end of the measuring tube communicates with a horn for deviating air flow in the measuring tube towards a side.

* * * * *